United States Patent
Amar et al.

(10) Patent No.: US 9,820,926 B2
(45) Date of Patent: Nov. 21, 2017

(54) COSMETIC OR DERMATOLOGICAL COMPOSITION FOR HYDRATING SKIN

(75) Inventors: David Amar, Mumbai (IN); Mayumi Takanuki, Tokyo (JP)

(73) Assignee: L'OREAL, Paris (FR)

( * ) Notice: Subject to any disclaimer, the term of this patent is extended or adjusted under 35 U.S.C. 154(b) by 45 days.

(21) Appl. No.: 14/425,140

(22) PCT Filed: Sep. 4, 2012

(86) PCT No.: PCT/JP2012/073005
§ 371 (c)(1),
(2), (4) Date: Aug. 25, 2015

(87) PCT Pub. No.: WO2014/038078
PCT Pub. Date: Mar. 13, 2014

(65) Prior Publication Data
US 2016/0000677 A1  Jan. 7, 2016

(51) Int. Cl.
*A61K 8/44* (2006.01)
*A61K 8/60* (2006.01)
*A61Q 19/00* (2006.01)
*A61K 8/34* (2006.01)

(52) U.S. Cl.
CPC .............. *A61K 8/442* (2013.01); *A61K 8/345* (2013.01); *A61K 8/60* (2013.01); *A61Q 19/007* (2013.01); *A61K 2800/592* (2013.01)

(58) Field of Classification Search
CPC ..... F24H 1/142; H05B 2203/021; H05B 3/44; A61K 2800/592; A61K 8/345; A61K 8/442; A61K 8/60; A61Q 19/007
See application file for complete search history.

(56) References Cited

U.S. PATENT DOCUMENTS

| | | | | |
|---|---|---|---|---|
| 5,688,493 A | * | 11/1997 | Sugawara | A61K 8/0212 424/489 |
| 8,501,162 B2 | * | 8/2013 | Barton | A61K 8/498 424/59 |
| 2010/0215603 A1 | | 8/2010 | Kanda et al. | |

FOREIGN PATENT DOCUMENTS

| | | | | |
|---|---|---|---|---|
| EP | 1891924 A1 | | 2/2008 | |
| JP | 02-295912 A | | 12/1990 | |
| JP | 2002-060335 | * | 2/2002 | ............... A61K 7/48 |
| JP | 2008-231034 A | | 10/2008 | |
| JP | 2008-290987 A | | 12/2008 | |
| JP | 2010-215556 A | | 9/2010 | |
| JP | 2011-26261 | * | 2/2011 | ............... A61K 8/34 |
| JP | 2011-026261 A | | 2/2011 | |
| JP | 4911720 B2 | | 4/2012 | |
| JP | 2012-162499 A | | 8/2012 | |
| WO | WO2009044190 | * | 4/2009 | ............... A61K 8/97 |

OTHER PUBLICATIONS

JP2012162499 English machine translation. Translated: 21:49:03 JST Jul. 14, 2016, 21 pages.*
JP2008290987 English machine translation. Translated: 21:44:20 JST Jul. 14, 2016, 19 pages.*
JP2011-26261 English machine translation. Feb. 10, 2011. 6 pages.*
JP2002-26261 English abstract. Feb. 2002. 1 page.*
International Search Report and Written Opinion for PCT/JP2012/073005, dated Jul. 3, 2013.
English language abstract for JP 02-295912 (Dec. 6, 1990).
English language abstract for JP 2008-290987 (Dec. 4, 2008).
English language abstract for JP 2011-026261 (Feb. 10, 2011).
English language abstract for JP 2012-162499 (Aug. 30, 2012).
Chinese First Office Action for related Chinese Application No. 201280076340.1, dated May 5, 2016 (with English translation).
Japanese Office Action for counterpart Japanese Application No. 2015-529213, dated Aug. 8, 2016 with translation.

* cited by examiner

*Primary Examiner* — Marcela M Cordero Garcia
(74) *Attorney, Agent, or Firm* — The Marbury Law Group, PLLC

(57) ABSTRACT

The present invention relates to a cosmetic composition, comprising: (a) at least one compound having a specific chemical structure with two or more fatty amide groups; (b) at least one monosacharide. The cosmetic composition according to the present invention can have superior skin hydration effects because the hydration effect of each of the components (a) and (b) is synergistically enhanced by the combination of the components (a) and (b).

13 Claims, No Drawings

COSMETIC OR DERMATOLOGICAL COMPOSITION FOR HYDRATING SKIN

This is a national stage application of PCT/JP2012/073005, filed internationally on Sep. 4, 2012.

TECHNICAL FIELD

The present invention relates to a cosmetic or dermatological composition, in particular for the skin, with enhanced hydration properties.

BACKGROUND ART

The skin of the body and more particularly that of the face is constantly subjected to environmental attacks, such as from wind, cold or dust, leading to a significant water loss from the skin which must be continuously compensated for. Dehydration of the skin is reflected by skin which is often wrinkled, harsh and rough, which has a tendency to desquamate and which has lost its elasticity. In addition, dehydration, except in the case of skin diseases, is often synonymous with aged skin. However, there is an increasing desire for one's skin to appear young and less wrinkled.

Many cosmetic or dermatological compositions which are on the market are intended for the treatment of dry skin or skin with a dry tendency. To achieve this, these compositions contain moisturizing active ingredients, such as polyols (glycerol), which unfortunately often confer a sticky feel to these compositions, thus deterring many consumers from using them. They can also contain hydroxy acids and/or their salts, which have the disadvantage of stinging, irritating and warming the skin, which results in a certain degree of discomfort for the user. There also exist compositions which contain oils or other fatty substances as moisturizing active ingredients or active ingredients which prevent dehydration, resulting in compositions which often take a long time to penetrate into the skin and which leave a greasy film on the skin, which is also not appreciated by users.

There is consequently an ongoing search to introduce into cosmetic or dermatological compositions new moisturizing active ingredients or active ingredients which prevent dehydration of the skin and seek to achieve restoration of its barrier effect to environmental attacks.

For example, JP-A-2011-26261 discloses a pack cosmetic containing water-soluble polymer, di-fatty acid acyl glutamic acid lysine salt (or di-fatty amide diglutamide lysine salt), in particular PELLICER L-30 (marketed by Asahi Chemicals), wax and polyhydric alcohol. This pack has a good spread and a good feeling of use without stickiness, and gives a moisture-retaining effect.

DISCLOSURE OF INVENTION

However, it has been discovered that a compound having a specific chemical structure with two or more fatty amide groups, such as di-fatty amide diglutamide lysine salt, itself has no hydration effect for keratin substances such as skin.

An objective of the present invention is to provide a cosmetic or dermatological composition including a compound having a specific chemical structure with two or more fatty amide groups, with improved or enhanced hydration ability for the keratin substance, preferably skin.

Another objective of the present invention is to provide a cosmetic method for providing the keratin substance with improved or enhanced moisturizing effects.

The above objectives of the present invention can be achieved by a cosmetic or dermatological composition, comprising:

(a) at least one compound represented by the formula (A):

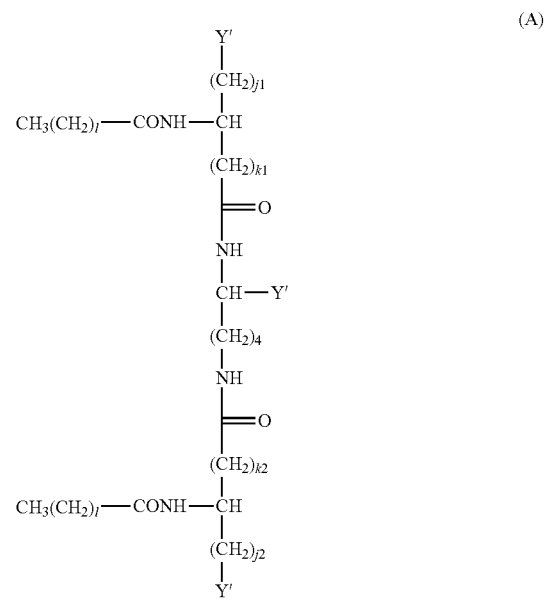

wherein

Y' independently denotes a carboxylic acid group or an alkaline salt of a carboxylic acid group such as a sodium salt of a carboxylic acid group, j1, k1, j2 and k2 denote an integer such that (j1, k1, j2, k2)=any of (2, 0, 2, 0), (2, 0, 0, 2), (0, 2, 2, 0) and (0, 2, 0, 2), and l denotes an integer from 6 to 16; and (b) at least one monosaccharide.

It is preferable that the amount of the (a) compound be 0.01 to 20% by weight, preferably 0.1 to 10% by weight and more preferably 0.2 to 5% by weight relative to the total weight of the composition.

It is preferable that the (b) monosaccharide be selected from $C_x(H_2O)_x$ wherein x denotes an integer of 3 to 7, and preferably is equal to 6.

It is preferable that the (b) monosaccharide be selected from hexoses and deoxyhexoses.

It is preferable that the (b) monosaccharide be selected from the group consisting of glucose, mannose, galactose, fructose, tagatose, rhamnose, and a mixture thereof.

It is preferable that the (b) monosaccharide be selected from the group consisting of mannose, rhamnose, and a mixture thereof.

Most preferably, the (b) monosaccharide is mannose.

It is preferable that the amount of the (b) monosaccharide be 0.01 to 20% by weight, preferably 0.1 to 10% by weight and more preferably 0.5 to 6% by weight relative to the total weight of the composition.

It is preferable that the cosmetic or dermatological composition according to the present invention be intended for moisturizing the skin.

It is preferable that the cosmetic or dermatological composition according to the present invention comprise less than 0.1% by weight relative to the total weight of the composition of a sugar alcohol, or comprise no sugar alcohol. The sugar alcohol may be sorbitol.

The present invention also relates to a cosmetic method for moisturizing a keratin substance such as skin, comprising the application onto the keratin substance of a cosmetic composition according to the present invention as mentioned above.

BEST MODE FOR CARRYING OUT THE INVENTION

After diligent research, the inventors have discovered that it is possible to provide a cosmetic or dermatological composition including a compound having a specific chemical structure with two or more fatty amide groups, with improved or enhanced hydration ability, as well as a cosmetic method for providing the skin with improved or enhanced moisturizing effects, by combining the above compound with at least one monosaccharide.

It is surprising that the hydration effects for a keratin substance such as skin are synergistically enhanced by a combination of the above compound with two or more fatty amide groups with monosaccharide. The monosaccharide itself has some hydration effects. However, due to the combination with the above compound, the hydration effects are synergistically enhanced or increased. This is completely beyond the expectation of a person skilled in the art because the above compound itself does not show any hydration effect for the skin.

Hereinafter, the cosmetic or dermatological composition according to the present invention will be explained in a more detailed manner. In the following description, the expression "at least one" is equivalent to the expression "one or several".

(Cosmetic or Dermatological Composition)

The composition according to the present invention relates to a topical composition which can be used for beautifying or treating a keratin substance such as skin, in particular dry skin. Thus, the composition according to the present invention is a cosmetic or dermatological composition. It is preferable that the cosmetic or dermatological composition according to the present invention be intended to moisturize a keratin substance such as skin, in particular dry skin.

(1) Compound with Two or More Fatty Amide Groups

The cosmetic or dermatological composition according to the present invention comprises at least one compound with two or more fatty amide groups (hereafter, it may be referred to as "amide compound"). Two or more amide compounds may be used in combination. Thus, a single type of amide compound or a combination of different types of amide compounds may be used.

It is preferable that the amide compound be represented by the following formula (A):

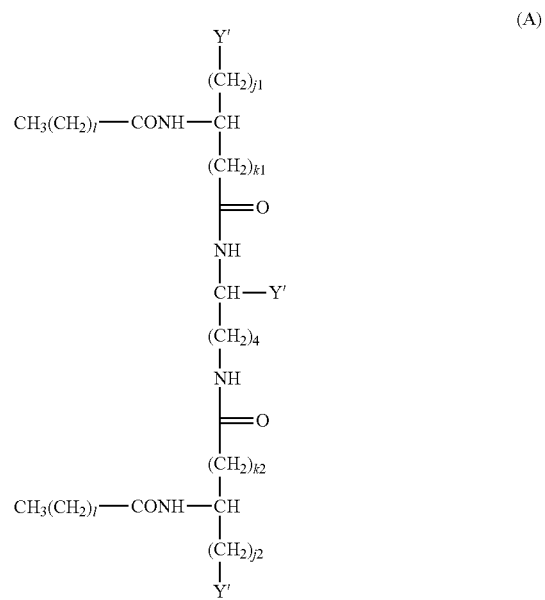

wherein

Y' independently denotes a carboxylic acid group or an alkaline salt of a carboxylic acid group such as a sodium salt of a carboxylic acid group, j1, k1, j2 and k2 denote an integer such that (j1, k1, j2, k2)=any of (2, 0, 2, 0), (2, 0, 0, 2), (0, 2, 2, 0) and (0, 2, 0, 2), and l denotes an integer from 6 to 16, preferably 8 to 14, and more preferably 10 to 12.

Preferably, in formula (A), L denotes an integer from 8 to 12, j1=j2=0, and k1=k2=2.

Most preferably, in formula (A), Y' is —COONa, j1=j2=0, k1=k2=2; and L=10.

As the amide compound, mention may be made of sodium dilauramidoglutamide lysine, sodium dimyristoylglutamide lysine, and sodium distearoylglutamide lysine. Sodium dilauramidoglutamide lysine is in particular preferable. Sodium dilauramidoglutamide lysine is marketed as PELLICER L-30 by Asahi Chemicals as an aqueous solution at a concentration of 29% by weight relative to the total weight of the aqueous solution.

The amide compound can be prepared by, for example, reacting a long chain N-acyl acidic amino acid anhydride with a basic amino acid, such as lysine, in water and/or a mixed solvent of water and organic solvent(s), or in inert organic solvent(s) such as tetrahydrofuran, benzene, toluene, xylene tetrachloromethane, chloroform, acetone or the like, or without any solvent, at −5° C. to 200° C., preferably 5° C. to 100° C., and more preferably 0° C. to 60° C.

The amount of the amide compound used in the cosmetic or dermatological composition according to the present invention is not limited. It is preferable that the amount of the acyl compound be 0.01 to 20% by weight, preferably 0.1 to 10% by weight and more preferably 0.2 to 5% by weight relative to the total weight of the composition.

(2) Monosaccharide

The cosmetic or dermatological composition according to the present invention comprises at least one monosaccharide. Two or more monosaccharides may be used in combination. Thus, a single type of monosaccharide or a combination of different types of monosaccharide may be used.

It is possible that the monosaccharide be selected from $C_x(H_2O)$, wherein x denotes an integer of 3 to 7, and preferably is equal to 6.

C3 monosaccharides (C3-trioses) may be aldotriose such as glyceraldehyde and ketotriose such as dihydroxyacetone.

C4 monosaccharides (C4-tetroses) may be aldotetrose such as erythrose and threose, and ketotetrose such as erythrulose.

C5 monosaccharides (C5-pentoses) may be aldopentose such as ribose, arabinose, xylose and lyxose, ketopentose such as ribulose and xylulose, and deoxypentose such as deoxyribose.

C6 monosaccharides (C6-hexoses) may be aldohexose such as allose, altrose, glucose, mannose, gulose, idose, galactose and talose, ketohexose such as pricose, fructose, sorbose and tagatose, deoxyhexose such as fucose, fructose and rhamnose.

C7 monosaccharides (C7-peptoses) may be sedoheptulose.

It is preferable that the monosaccharide be selected from hexoses and deoxyhexoses.

It is preferable that the monosaccharide be selected from the group consisting of allose, altrose, glucose, mannose, gulose, idose, galactose, talose, sorbose, psicose, fructose, tagatose and rhamnose. It is more preferable that the monosaccharide be selected from the group consisting of glucose, mannose, galactose, fructose, tagatose, rhamnose, and a mixture thereof. It is further more preferable that the monosaccharide be selected from the group consisting of mannose, rhamnose, and a mixture thereof.

The amount of the monosaccharide used in the cosmetic or dermatological composition according to the present invention is not limited. It is preferable that the amount of the monosaccharide be 0.01 to 20% by weight, preferably 0.1 to 10% by weight and more preferably 0.5 to 6% by weight relative to the total weight of the composition.

Preferably, the composition according to the present invention contains the (a) amide compound and the (b) monosaccharide in a weight ratio of the (b) monosaccharide/ the (a) amide compound {(b)/(a)}ranging from 14 to 25, preferably from 14 to 20.

(3) Sugar Alcohols

It is preferable that the cosmetic or dermatological composition according to the present invention not contain a substantial amount of any sugar alcohol. In an embodiment, it is possible that the cosmetic or dermatological composition according to the present invention contain less than 0.1% by weight relative to the total weight of the composition of a sugar alcohol, or not comprise any sugar alcohol.

As examples of the sugar alcohol, mention may be made of sugar alcohols having 4 carbon atoms such as erythritol, threitol, and the like; sugar alcohols having 5 carbon atoms such as arabinitol, xylitol, ribitol, and the like; and sugar alcohols having 6 carbon atoms such as iditol, garactirol, sorbitol, mannitol, and the like.

It is preferable that the cosmetic or dermatological composition according to the present invention contain less than 0.1% by weight relative to the total weight of the composition of sorbitol, or not comprise any sorbitol.

(4) Other Components

The cosmetic or dermatological composition according to the present invention may comprise an aqueous medium.

The aqueous medium in the cosmetic or dermatological composition according to the present invention comprises water. The amount of water may be less than 95 wt %, preferably 50 wt % to 95 wt %, more preferably 55 wt % to 90 wt %, even more preferably 60 wt % to 85 wt %, relative to the total weight of the composition.

The aqueous phase may further comprise at least one organic solvent. So the organic solvent is preferably water miscible at room temperature (25° C.). As the organic solvent, there may be mentioned, for example, $C_2$-$C_4$ monoalkanols, such as ethanol and isopropanol; polyols preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$) alkyl ethers, and mono-, di- or triethylene glycol ($C_1$-$C_4$) alkyl ethers; and mixtures thereof, such as monomethyl ether of propylene glycol, monoethyl ether, and monomethyl ether of diethylene glycol.

The organic water-soluble solvents may be present in an amount ranging from 1 to 40 wt %, preferably from 1 to 30 wt %, and more preferably from 5 to 20 wt %, relative to the total weight of the composition.

The pH of the cosmetic or dermatological composition according to the present invention may be generally, for example, from 4 to 12. It can range from 6 to 12, preferably 7 to 11, and may be adjusted to the desired value using at least one acidifying agent that is well-known in the prior art.

The acidifying agents can be, for example, mineral or organic acids, for instance, hydrochloric acid and orthophosphoric acid, carboxylic acids, for instance, tartaric acid, citric acid, and lactic acid, or sulphonic acids.

The viscosity of the cosmetic or dermatological composition according to the present invention is not particularly limited. The viscosity can be measured at 25° C. with viscosimeters or rheometers preferably with cone-plane geometry. Preferably, the viscosity of the cosmetic or dermatological composition according to the present invention can range, for example, from 1 to 2000 Pa·s, and preferably from 1 to 1000 Pa·s at 25° C. and 1 $s^{-1}$.

The cosmetic or dermatological composition according to the present invention is in the form of an emulsion, preferably in the form of an oil-in-water emulsion. Hereinafter, a preferable embodiment of the composition according to the present invention which is in the form of an oil-in-water emulsion is described.

The composition may comprise at least one oil.

The amount of the oil(s) is not limited, and it can be present in an amount of less than 50 wt % relative to the total weight of the composition. The amount of the oil(s) can range, for example, from 0.1 to 50 wt %, preferably from 0.5 to 45 wt %, more preferably 1 to 40 wt % relative to the total weight of the composition.

The term "oil" is intended to mean a fatty substance that is liquid at ambient temperature (25° C.).

As the other oil(s), mention may in particular be made of esters of molecular weight less than 360 g/mol, such as 2-ethylhexyl caprate/caprylate (or octyl caprate/caprylate), ethyl laurate, butyl laurate, hexyl laurate, isohexyl laurate, isopropyl laurate, methyl myristate, ethyl myristate, butyl myristate, isobutyl myristate, isopropyl myristate, 2-ethylhexyl monococoate (or octyl monococoate), methyl palmitate, ethyl palmitate, isopropyl palmitate, isobutyl palmitate, butyl stearate, isopropyl stearate, isobutyl stearate, isopropyl isostearate, 2-ethylhexyl pelargonate (or octyl pelargonate) 2-ethylhexyl hydroxystearate (or octyl hydroxystearate), decyl oleate, diisopropyl adipate, 2-diethylhexyl adipate (or dioctyl adipate), diisocetyl adipate, 2-ethylhexyl succinate (or octyl succinate), diisopropyl sebacate, 2-ethylhexyl malate (or octyl malate), pentaerythritol caprate/caprylate, 2-ethylhexyl hexanoate, (or octyl hexanoate), octyldodecyl octanoate, isodecyl neopentanoate, isostearyl neopentanoate, isononyl isononanoate, isotridecyl isononanoate, lauryl lactate, myristyl lactate, cetyl lactate, myristyl propionate, 2-ethylhexyl 2-ethylhexanoate (or octyl 2-ethylhexanoate), 2-ethylhexyl octanoate (or octyl octanoate), and mixtures thereof; isopropyl lauroyl sarcosinate (Eldew SL 205 from Unipex), dicaprylyl carbonate (Cetiol CC from Cognis); ethers such as dicaprylyl ether (Cetiol OE from Cognis); hydrocarbon-based oils of plant origin, such as sweet almond oil, avocado oil, castor oil, coriander oil, olive oil, jojoba oil, sesame oil, groundnut oil, grapeseed oil, rape seed oil, coconut oil, hazelnut oil, shea butter, palm oil, apricot kernel oil, beauty-leaf oil, rice bran oil, corn germ oil, wheat germ oil, soybean oil, sunflower oil, evening primrose oil, safflower oil, passion flower oil, rye oil, caprylic/capric acid triglycerides such as those sold by the company Stearineries Dubois or those sold under the names Miglyol 810, 812 and 818 by the company Dynamit Nobel; volatile or non-volatile silicone oils, such as volatile or non-volatile polydimethylsiloxanes (PDMS) containing a linear or cyclic silicone chain, that are liquid or pasty at ambient temperature, in particular cyclopolydimethylsiloxanes (cyclomethicones) such as cyclohexasiloxane; polydimethylsiloxanes containing alkyl, alkoxy or phenyl groups that are pendent or at the end of the silicone chain, which groups have from 2 to 24 carbon atoms; phenyl silicones such as phenyl trimethicones, phenyl dimethicones, phenyltrimethyl-siloxydiphenylsiloxanes, diphenyl dimethicones, diphenylmethyldiphenyltrisiloxanes, 2-phenylethyltrimethyl siloxysilicates, polymethylphenylsiloxanes; fluoro oils such as those that are partially hydrocarbon-based and/or silicone based, for instance those described in document JP-A-2-295912;

linear or branched hydrocarbon-based oils of mineral, synthetic or animal origin, chosen from isohexadecane, isododecane, $C_{8-9}$ and $C_{11-13}$ isoparaffins (CTFA name: $C_{8-9}$ Isoparaffin and $C_{11-13}$ Isoparaffin); and mixtures thereof.

The cosmetic or dermatological composition according to the present invention may also comprise an effective amount of cosmetic additives such as surfactants, thickeners, sequestering agents, UV screening agents, preserving agents, vitamins or provitamins, opacifiers, fragrances, plant extracts, humectants, waxes, fillers, colouring materials, antioxydants, proteins, and so on.

The cosmetic or dermatological composition according to the present invention can be prepared by mixing (a) at least one compound according to the above general formula (1), and (b) at least one monosaccharide, as well as other optional ingredients as described above.

(Cosmetic Method)

The cosmetic composition according to the present invention can be used in a cosmetic method containing the step of applying the cosmetic composition onto a keratin substance. The keratin substance here means a material containing keratin as a main constituent element, and examples thereof include skin, nails, lips, and the like.

The cosmetic method according to the present invention is for moisturizing a keratin substance such as skin comprising the application on the keratin substance of a cosmetic composition as explained above. Thus, the cosmetic method according to the present invention has an aspect of a moisturizing process for the skin.

The cosmetic method according to the present invention is preferably used for hydrating the skin, in particular the face. Preferably, the cosmetic method according to the present invention can be used for treating dry skin.

Therefore, the cosmetic method according to the present invention can be used for treating dry skin and/or lips, preferably cosmetically treating dry skin and/or lips, which comprises topically applying to said dry skin and/or lips the cosmetic composition according to the present invention.

Alternatively, the cosmetic method according to the present invention can be used for hydrating skin and/or lips, in particular dry skin and/or lips, which comprises topically applying to said skin and/or lips the cosmetic composition according to the present invention.

EXAMPLES

The present invention will be described in more detail by way of examples, which however should not be construed as limiting the scope of the present invention.

The cosmetic compositions with the formulations shown in Table 1 were prepared as shown below by mixing the components shown in Table 1. The numerical values for the amounts of the components shown in Table 1 are all based on "% by weight" as active raw materials.

TABLE 1

| Phase | | Ex. 1 | Comp. Ex. 1 | Comp. Ex. 2 | Comp. Ex. 3 |
|---|---|---|---|---|---|
| A1 | Water | 22.0 | 22.0 | 22.0 | 22.0 |
| | Mannose | 5.0 | 5.0 | — | — |
| | PEG-20 Methyl Glucose Sesquistearate (Glucamate SSE-20 from Lubrizol) | 0.1 | 0.1 | 0.1 | 0.1 |
| | Octyldodecanol | 0.5 | 0.5 | 0.5 | 0.5 |
| A2 | Caprylylglycol | 0.3 | 0.3 | 0.3 | 0.3 |
| | Phenoxyethanol | 0.5 | 0.5 | 0.5 | 0.5 |
| | Disodium EDTA | 0.1 | 0.1 | 0.1 | 0.1 |
| | Citric acid | 0.015 | 0.015 | 0.015 | 0.015 |
| | Water | 63.735 | 64.735 | 68.735 | 69.735 |
| A3 | Sodium Dilauramido Glutamide Lysine in aqueous solution with a concentration of 29% by weight (Pellicer L-30 from Asahi Kasei Chemicals) | 1.0 | — | 1.0 | — |
| B | Sodium Hyaluronate (Crystalhyal from Soliance) | 0.4 | 0.4 | 0.4 | 0.4 |
| | Ammonium Polyacryloyl-dimethyltaurate (Hostacerin AMPS ® from Clariant) | 0.25 | 0.25 | 0.25 | 0.25 |
| | Xanthan Gum (Keltrol CGT from Kelco) | 0.1 | 0.1 | 0.1 | 0.1 |
| C | Dimethicone 100 cst | 1.0 | 1.0 | 1.0 | 1.0 |
| D | Ethanol | 5.0 | 5.0 | 5.0 | 5.0 |
| Initial Hydration Level (T0) | | 31.942 | 32.101 | 31.913 | 29.797 |
| 1 Hour Later Hydration Level (T1) | | 36.536 | 35.667 | 34.217 | 32.232 |
| Hydration Effect (T1-T0) | | 4.594 | 3.566 | 2.304 | 2.435 |
| Relative Hydration Level | | 2.159 | 1.131 | −0.131 | 0 |

[Preparations]

(1) The components of the above phase A1 in Table 1 were heated up to 60 to 70° C., and mixed. The components of the above phase A2 in Table 1 were heated separately up to 60 to 70° C., and mixed.

(2) The mixture of the components of the phase A1 was added to the mixture of the components of the phase A2, and mixed.

(3) The component of the above phase A3 in Table 1 was added to the mixture obtained in the above step (2), and the mixture was homogenized with a homogenizer at 7000 rpm for 7 minutes.

(4) The components of the above phases B and C were added to the mixture obtained in the above step (3).

(5) The mixture obtained in the above step (4) was cooled to room temperature, and the component of the above phase D was added to the mixture.

[Evaluations]

For the cosmetic compositions according to Example 1 and Comparative Examples 1 to 3, hydration effects were determined as follows.

The hydration conditions of the skin of the inside forearm of 24 female panels were measured with a Corneometer® CM825 (from Courage+Khazaka Electronic GmbH). The Corneometer is a well-known and standard skin hydration measurement device which has been used in numerous dermatology and cosmetology literature for skin hydration measurements. The measurement results are shown as "Initial Hydration Level (T0)" in Table 1. The Corneometer® CM 825 measures the change in the dielectric constant due to skin hydration changing the capacitance of a precision capacitor. Units of the measure are arbitrary Corneometer® units ranging from 0 to 130.

Each of the cosmetic compositions according to Example 1 and Comparative Examples 1 to 3 was applied on the skin of the inside forearm of 24 female panels in an amount of 2 mg/cm$^2$. One hour later, the hydration conditions of the skin, to which the cosmetic composition had been applied, were measured again with the same Corneometer® CM825. The measurement results are shown as "1 Hour Later Hydration Level (T1)" in Table 1.

The change in the hydration conditions before and after the application of the cosmetic composition, i.e., "1 Hour Later Hydration Level (T1)"–"Initial Hydration Level (T0)" in Table 1, is determined as the hydration effect shown as "Hydration Effect" in Table 1.

The hydration effects of the cosmetic compositions according to Example 1 and Comparative Examples 1 to 3 are compared, under the conditions that the hydration effect of the cosmetic composition according to Comparative Example 3 is 0, as shown in the line of Relative Hydration Level in Table 1.

As shown in Table 1, Comparative Example 1 including monosaccharide shows some hydration effects as compared to Comparative Example 3. On the other hand, Comparative Example 2 including only a compound represented by the formula (1) shown in Claim 1 does not show any hydration effects, as compared to Comparative Example 3. However, by combining monosaccharide and the above compound represented by the formula (1), the hydration effects are synergistically enhanced as shown by Example 1 in Table 1.

Relative Hydration Level of Comparative Example 2 (Pellicer L-30 alone)=Hydration Effect of Comparative Example 2 (2.304)–Hydration Effect of Comparative Example 3 (2.435)=–0.131

Relative Hydration Level of Comparative Example 1 (Mannose alone)=Hydration Effect of Comparative Example 1 (3.566)–Hydration Effect of Comparative Example 3 (2.435)=1.131

Relative Hydration Level of Example 1 (Pellicer L-30+Mannose)=Hydration Effect of Example 1 (4.594)–Hydration Effect of Comparative Example 3 (2.435)=2.159

Relative Hydration Level of Example 1 (2.159) is higher than the sum of Relative Hydration Levels of Comparative Example 2 (Pellicer L-30 alone) (–0.131) and of Comparative Example 1 (Mannose alone) (1.131). The experimental data in Table 1 shows synergistic hydration effects by the combination of Pellicer L-30 and mannose.

The invention claimed is:

1. A process for moisturizing skin or lips, comprising applying onto the skin or lips, a composition comprising:
   (a) at least one compound of formula (A):

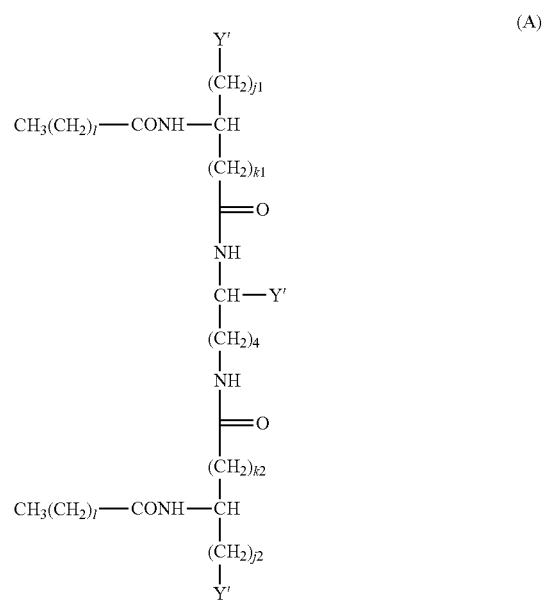

wherein

Y' is a carboxylic acid group or an alkaline salt of a carboxylic acid group, j1, k1, j2 and k2 are each an integer such that (j1, k1, j2, k2) is equal to any of the sequences (2, 0, 2, 0), (2, 0, 0, 2), (0, 2, 2, 0) and (0, 2, 0, 2), and l is an integer ranging from 6 to 16; and (b) at least one monosaccharide chosen from mannose, galactose, tagatose, rhamnose, or mixtures thereof;

wherein the combination of components (a) and (b) provides enhanced moisturizing effects to said skin or lips.

2. The process according to claim 1, wherein the at least one compound of formula (A) is present in the composition in an amount ranging from 0.01% to 20% by weight, relative to the total weight of the composition.

3. The process according to claim 1, wherein the at least one compound of formula (A) is present in the composition in an amount ranging from 0.1% to 10% by weight, relative to the total weight of the composition.

4. The process according to claim 1, wherein the at least one compound of formula (A) is present in the composition an amount ranging from 0.2% to 5% by weight, relative to the total weight of the composition.

5. The process according to claim 1, wherein the at least one monosaccharide is mannose.

6. The process according to claim 1, wherein the at least one monosaccharide is present in the composition in an amount ranging from 0.01% to 20% by weight, relative to the total weight of the composition.

7. The process according to claim 1, wherein the composition further comprises a sugar alcohol.

8. The process according to claim 7, wherein the sugar alcohol is present in the composition in an amount less than 0.1% by weight, relative to the total weight of the composition.

9. The process according to claim 7, wherein the sugar alcohol is sorbitol.

10. The process according to claim 1, wherein Y' in formula (A) is a carboxylic acid group or a sodium salt of a carboxylic acid group.

11. The process according to claim 1, wherein the at least one compound of formula (A) is chosen from dilauramidoglutamide lysine, sodium dimyristoylgutamide lysine, or sodium distearoylglutamide lysine.

12. The process according to claim 1, wherein the at least one compound of formula (A) is dilauramidoglutamide lysine.

13. The process according to claim 1, wherein the skin is dry skin.

* * * * *